United States Patent

Mittelstadt et al.

[11] Patent Number: 5,982,532
[45] Date of Patent: Nov. 9, 1999

[54] PROCESS FOR THE OPERATION OF AN OPERATION MICROSCOPE

[75] Inventors: Walter Mittelstadt, Konigsbronn; Manfred Knoll, Abtsgmund; Joachim Luber, Essingen-Forst; Arvids Mackevics, Aalen-Waldhausen; Christian Duschek, Heuchlingen, all of Germany

[73] Assignee: Carl Zeiss-Stiftung, Germany

[21] Appl. No.: 08/730,248

[22] Filed: Oct. 15, 1996

[30] Foreign Application Priority Data

Oct. 12, 1995 [DE] Germany .......................... 195 37 974

[51] Int. Cl.⁶ ........................... G02B 21/18; G02B 27/10
[52] U.S. Cl. .............................................................. 359/368
[58] Field of Search .................................. 359/368, 382, 359/383, 384, 630

[56] References Cited

U.S. PATENT DOCUMENTS

| | | |
|---|---|---|
| 4,671,771 | 6/1987 | LaRussa et al. ........................... 434/22 |
| 4,722,056 | 1/1988 | Roberts et al. .......................... 364/413 |
| 4,815,832 | 3/1989 | Nagano et al. .......................... 359/384 |
| 4,912,388 | 3/1990 | Tanaka et al. ........................... 359/382 |
| 4,988,111 | 1/1991 | Gerlizt et al. ............................. 434/22 |
| 5,261,404 | 11/1993 | Mick et al. ........................... 128/653.1 |
| 5,579,048 | 11/1996 | Hirasawa ................................. 348/333 |
| 5,697,368 | 12/1997 | Luber et al. ........................ 128/653.1 |

*Primary Examiner*—Jon Henry

[57] ABSTRACT

In an operation microscope (1) with an integrated navigation system (3), the control of the navigation system (3) takes place by means of an operating unit (5, 7, 9) that can be operated directly from the operation microscope (1) and which acts on a navigation system control menu (11) that is reflected into the visual field of the operation microscope (1).

11 Claims, 2 Drawing Sheets

PROCESS FOR THE OPERATION OF AN OPERATION MICROSCOPE

BACKGROUND OF THE INVENTION

1. Field of the Invention

The present invention relates to an operation microscope with an integrated operation navigation system.

2. Description of Prior Art

Such an operation microscope is known from the brochure 30-280-e of the Carl Zeiss Company entitled "A New Perspective in Neurosurgery." With this operation microscope which is intended for neurosurgery, a surgical intervention can be planned on the basis of diagnostic data: for example, a target point, and an operation path to this target point, are established and stored. During the operation, the surgeon can then allow himself to be guided by the navigation system along the operation path which has been established to reach the target point. Orientation data in the form of navigation symbols which show the path are indicated by the reflection of a display screen into the visual field of the microscope. Such navigation symbols are, for example, small crosses which mark the planned operation path and/or the present focus point, directional arrows, data on distance to the target point, and so on.

It is also possible to plan and store several alternative operation paths, in order not to be constrained to a single path during the operation. A desired operation path can then be chosen by means of the navigation system and displayed in the visual field of the microscope. Moreover, the navigation system offers further aids to orientation, for example, contours of given brain structures which are reflected into the visual field in correct positions, and even offers the possibility of modifying the operation planning during the operation.

Detailed examples relating to the mode of operation of such an operation microscope with integrated navigation system are given in the German Patent Application P 44 16 229.4 of the Carl Zeiss Company.

In the operation microscope which is known from the brochure 30-280-d, the control of the navigation system, e.g., the changeover to another planned operation path or the activation of a contour representation, assisted by a display on the so-called work station, takes place in a planning and operating unit which is separate from the operation microscope proper. When the surgeon himself wishes to act on the navigation system to control it, he thus has to turn away from the operation microscope, and thus to interrupt his observation of the region of the operation. However, this is to be avoided exactly in those critical operative situations which require an effect on the operative navigation.

SUMMARY OF THE INVENTION

The object of this invention is to provide an operation microscope with integrated operation navigation system, in which the navigation system is controllable without interrupting the observation of the visual field of the microscope.

This object is attained according to the invention by an operating unit for controlling the navigation system that can be operated directly from operation microscope and which acts on a navigation system control menu that is reflected into a visual field of the operation microscope.

The surgeon can then, without having to turn his gaze from the visual field of the microscope, control or operate the navigation system with the navigation system operating unit, which can be operated directly from the operation microscope and which acts on the display of a control menu which is reflected into the visual field of the operation microscope.

The operating modes of the navigation system and the parameters associated with these operating modes, e.g., the operation path selection mode and the reference number of the desired operation path, are activated or selected by means of the control menu according to the invention.

When the operating unit is a manual control panel with press buttons, arranged directly on a handle of the operation microscope, or a foot control panel with a control column and/or press buttons, or responds to speech via a microphone, on the one hand an effective sterilization of the operating unit is then possible, and on the other hand, secure and uncomplicated manipulation of the operating unit is possible, even with a sterilizing sheath surrounding the operation microscope.

It is particularly advantageous to provide at least two operating units, for example, a foot control panel and a hand control panel, and/or an operating unit which responds to speech, since the surgeon then has an alternative possibility of at least one other operating unit, when he cannot immediately act on one of the operating units, e.g., when he cannot operate the operating unit which responds to speech during oral instructions to personnel assisting in the operation. The redundancy effected by this embodiment of the invention can of course be advantageous in the case of a breakdown.

A referencing operation mode of the navigation system can be activated by the operating unit, in which mode, by aiming at reference points associated with a patient, stored orientation data can be correlated with the present position of the patient. The navigation system can further assist the surgeon after a referencing, even when the position of the patient changes during the operation.

The operation microscope is distinguished by particular operator-friendliness, flexibility and versatility, since via the operating unit, operating modes of the navigation system to select an operation path, a diagnostic image and/or a contour representation can be activated. In these modes an operation path, a diagnostic image and/or a contour representation can be selected from plural stored operation paths, diagnostic images and/or contour representations.

BRIEF DESCRIPTION OF THE DRAWINGS

The following description of preferred embodiments serves to facilitate understanding of the invention, with reference to the accompanying drawings in which.

DETAILED DESCRIPTION OF PREFERRED EMBODIMENTS

Figure 1:
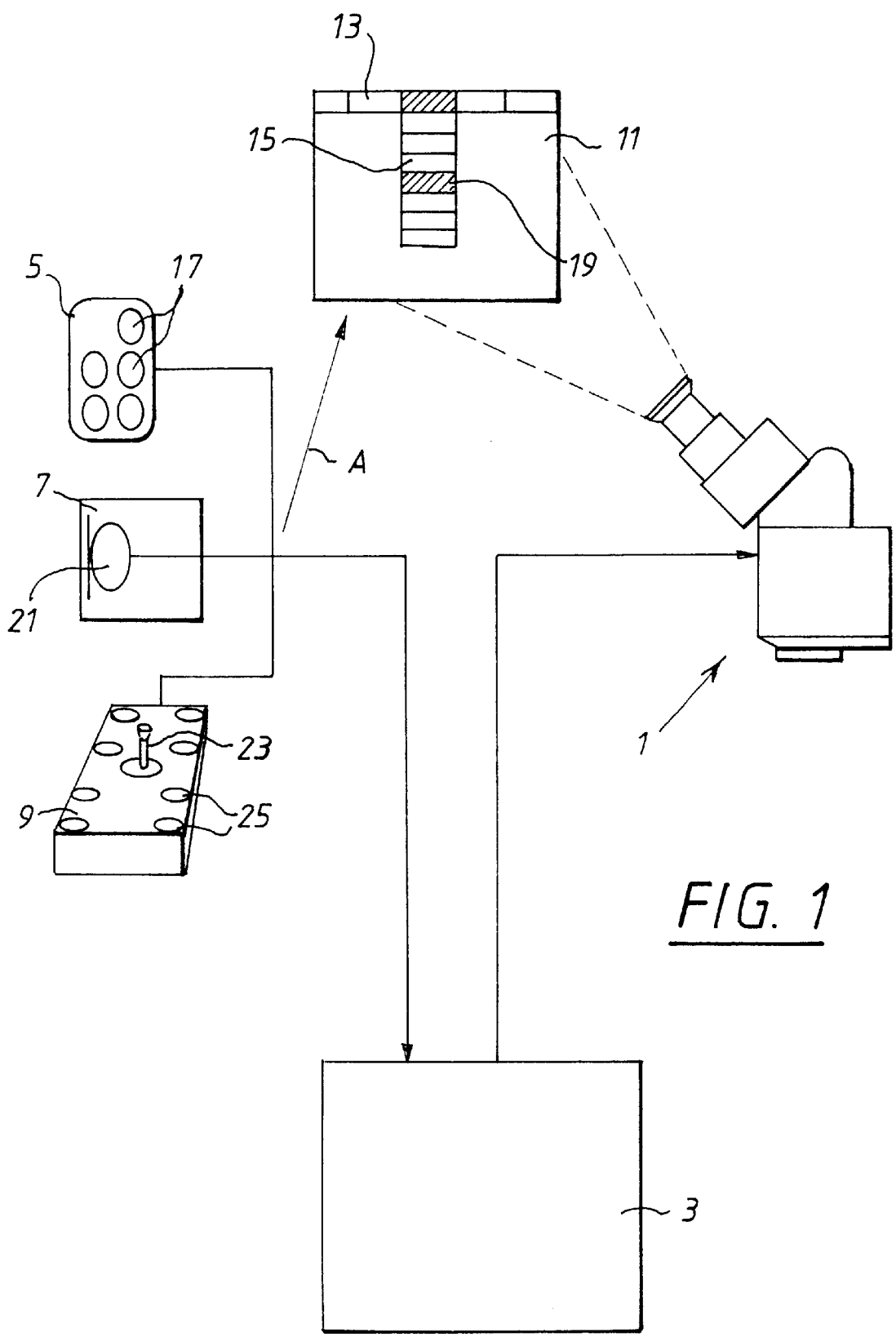
FIG. 1 shows a schematic representation of an operation microscope according to the invention.

The schematic representation of FIG. 1 shows the operation microscope according to the invention in the manner of a block circuit diagram. A computer supported navigation and orientation system 3, which is integrated into the operation microscope 1, leads the surgeon to the operation target during the operation by means of graphical and numerical information elements which are reflected into the visual field of the operation microscope 1, and assists him in orienting himself.

To control the navigation system 3, a series of operating units is provided, e.g., a manual control panel 5, an operating unit 7 which responds to speech, and a foot control panel 9. It is possible to provide on the operation microscope 1 only a single one of the three operating units 5, 7, 9 shown. However, it is preferable on the grounds of redundancy and servicing to provide at least two operating units. In this case, the respectively identical functions of the operating units can be connected in parallel, without being prioritized.

The operating units 5, 7, 9, via the navigation system 3, act on a navigation system control menu 11 which is reflected into the visual field of the operation microscope 1 via a display screen (not shown in the drawing); this is indicated symbolically by the two dashed lines. Here, the representation of the menu 11 includes the known interactive menu bar and "pull-down" structure with a menu bar 13 and "pull down" dialog windows 15.

Individual fields of the menu bar and "pull down" structure (the shaded field 19 in the example shown) can be activated by means of the five press buttons 17 of the manual control panel 5, or by a microphone 21 of the operating unit 7 which responds to speech, or by a control column 23 and press buttons 25. This control, proceeding in parallel with observation through the operating microscope 1, is symbolized by the arrow A.

The individual press buttons 17 of the manual control panel 5; the control column 23 and the press buttons 25 of the foot control panel 9; and the relays, simulating keys and actuated by voice commands of the operating unit 7 which responds to speech; are associated with menu functions. These menu functions include, e.g., the movement to the left and/or right on the menu bar 13, the movement up and/or down in the "pull down" structure 15, the activation of a selected menu field, exiting from the navigation system control mode, and switching on of the operating mode, in which the navigation system supports the surgeon in the known manner during the operation proper.

The functions of the navigation system 3 which are selectable in this manner include, e.g., a referencing mode, in which orientation information stored with the operation microscope before the operation is related to the actual position of the patient by aiming at reference points associated with the patient. For example, contours of a given brain structure can be reflected into the visual field in a correct position only after a referencing procedure. Further operating modes are, e.g., selection and display of a given operation path from plural stored paths, selection and display of contour representations which have been made available and stored preoperatively, and selection and display of diagnostic images which have been made available and recorded preoperatively. In addition, an operation path modification mode of the navigation system 3 can also be activated.

Figure 2:
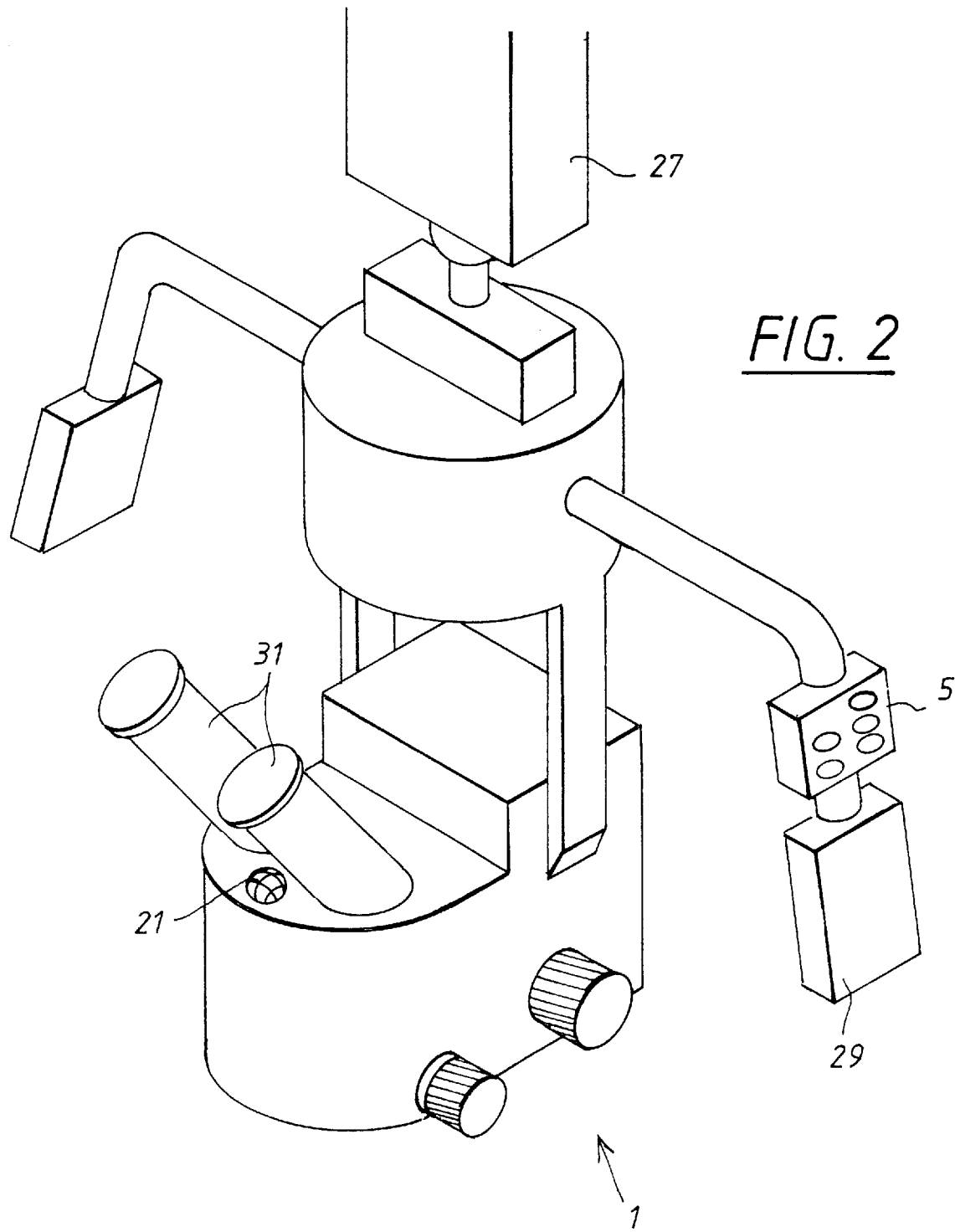
FIG. 2 shows a perspective view of an operation microscope according to the invention, with two operating units.

The operation microscope 1 is shown in perspective in FIG. 2. Also partially seen here is a stand 27 which makes possible the mobility of the operation microscope 1, and which can be moved under motorized control and also by the hand of the surgeon. The hand control panel 5 is arranged in the immediate vicinity of handle 29, so that the control buttons 17 are always in the surgeon's sphere of action. The microphone also, by its arrangement in the region of the eyepiece 31, is always located in the surgeon's sphere of action.

We claim:

1. An operation microscope (1) comprising:
   an integrated navigation system (3), and
   an operating unit (5, 7, 9) for controlling said navigation system (3) that is operable directly from said operation microscope (1) and acts on a navigation system control menu (11) that is reflected into a visual field of said operation microscope (1), said operating unit (5, 7, 9) comprising a plurality of individual operating elements (17, 23, 25) associated with individual menu functions of said navigation system control menu (11).

2. The operation microscope according to claim 1, wherein said operating unit includes a hand control panel (5) with press buttons (17) arranged directly on an operation microscope handle (29).

3. The operation microscope according to claim 1, wherein said operating unit includes a foot control panel (9) with a control column (23) and press buttons (25).

4. The operation microscope according to claim 1, wherein said operating unit (7) includes a microphone for responding to speech.

5. The operation microscope according to claim 1, comprising at least two operating units (5, 7, 9).

6. The operation microscope according to claim 1, wherein said operating unit (5, 7, 9) is arranged to activate a referencing operating mode of said navigation system (3) in which stored orientation information can be correlated with an actual position of a patient by aiming at reference points associated with the patient.

7. The operation microscope according to claim 1, wherein said operating unit (5, 7, 9) is arranged to activate an operation path selection operating mode of said navigation system in which an operation path is selectable from a plurality of stored operation paths.

8. The operation microscope according to claim 1, wherein said operating unit (5, 7, 9) is arranged to activate a diagnostic image selection operating mode of said navigation system (3) in which a diagnostic image is selectable from a plurality of stored diagnostic images.

9. The operation microscope according to claim 1, wherein said operating unit (5, 7, 9) is arranged to activate a contour image selection operating mode of said navigation system in which a contour image is selectable from a plurality of stored contour images.

10. The operation microscope according to claim 1, wherein said control menu (11) comprises menu fields and said menu functions comprise moving between said menu fields.

11. The operation microscope according to claim 1, wherein said control menu (11) comprises menu fields and said menu functions comprise selecting one of said menu fields and activating said selected menu field.

* * * * *